United States Patent [19]

Knell

[11] 3,956,412
[45] May 11, 1976

[54] PROCESS FOR THE ADDITION OF PERFLUOROALKYL IODIDES TO GASEOUS HALOGENATED OLEFINS

[75] Inventor: Martin Knell, Ossining, N.Y.

[73] Assignee: Ciba-Geigy Corporation, Ardsley, N.Y.

[22] Filed: Aug. 31, 1973

[21] Appl. No.: 393,355

Related U.S. Application Data

[63] Continuation of Ser. No. 159,513, July 2, 1971, abandoned, which is a continuation-in-part of Ser. No. 4,179, Jan. 1, 1970, abandoned, which is a continuation of Ser. No. 693,148, Dec. 26, 1967, abandoned.

[52] U.S. Cl............................................ 260/653.1 T
[51] Int. Cl.²..................................... C07C 17/28
[58] Field of Search ................ 260/653.1 T, 653.1, 260/653, 653.3

[56] References Cited
FOREIGN PATENTS OR APPLICATIONS
42-20782  10/1967  Japan........................... 260/653.1 T

*Primary Examiner*—D. Horwitz
*Attorney, Agent, or Firm*—Joseph G. Kolodny; Edward McC. Roberts; Prabodh I. Almaula

[57] ABSTRACT

Liquid perfluoroalkyl iodides are added to halogenated gaseous olefins in the presence of free radical generating catalysts. The gaseous olefin is bubbled through liquid perfluoroalkyl iodide and catalyst at temperatures of 50° to 220°C, and pressures no higher than atmospheric.

7 Claims, No Drawings

PROCESS FOR THE ADDITION OF PERFLUOROALKYL IODIDES TO GASEOUS HALOGENATED OLEFINS

RELATED APPLICATIONS

This invention is a continuation of Ser. No. 159,513, filed July 2, 1971, now abandoned, which is a continuation-in-part of Ser. No. 4,179 filed Jan. 1, 1970, now abandoned, which application in turn is a continuation of Ser. No. 693,148 filed Dec. 26, 1967 and now abandoned. Filed concurrently with Ser. No. 159,513 were two other continuations-in-part of Ser. No. 4,179 entitled Process for the Addition of Gaseous Non-Halogenated Olefins and Acetylenes to Perfluoroalkyl Iodides, Ser. No. 159,515, now abandoned, and Process for the addition of Gaseous Olefins and Acetylenes to Iodo Fluorinated Ethers, Ser. No. 159,514, now abandoned.

BACKGROUND OF THE INVENTION

This invention relates to an improved process for the addition reaction of halogenated hydrocarbon olefins with perfluoroalkyl iodides.

The present invention may be considered to be in a related area of technology as prior art patents, namely, Blanchard et al., U.S. Pat. No. 3,226,449, and Brace U.S. Pat. No. 3,145,222.

Blanchard et al., U.S. Pat. No. 3,226,449, employ starting materials of specific perfluoroalkyl iodides with tetrafluorethylene to obtain higher perfluoroalkyl iodides in the presence of a free radical generating catalyst.

The process of Blanchard et al teaches injecting during a reaction cycle tetrafluoroethylene and a free radical generating catalyst into liquid perfluoroethyl iodide and mixtures thereof with n-perfluorobutyl iodide. The liquid charge also contains the catalyst in a vessel maintained at a pressure between 225 psi to 700 psi at a temperature of 80° to 170°C. The reaction mixture products are of the structure $F(CF_2)_mI$ wherein $m$ is an even integer from 6 to 12.

The process disclosed by Blanchard et al represents a contribution to the art; however, several inherent limitations exist, namely:

1. Process is limited to a narrow range of source materials.
2. Process is limited to relatively high pressure conditions involving expensive equipment and hazardous reaction conditions.
3. Process is limited to production of telomers.

Brace, U.S. Pat. No. 3,145,222 discloses perfluoroalkyl iodides can be added to olefins in the presence of free radical generating catalysts in acceptable conversions and yields. The process disclosed by Brace in U.S. Pat. No. 3,145,222 is carried out at temperatures ranging from about 50° to about 190°C, depending primarily upon the specific free radical generating catalyst that is employed. If the olefin employed is a gas at reaction temperature and atmospheric pressure, then a super-atmospheric pressure system must be employed in the practice of the Brace process. This naturally adversely affects the economic feasibility of the process because of the expensive pressure equipment necessary to maintain the conditions and the complication involved thereby. Thus, for example, in order to adjust the concentration of the reactants, the pressure must be adjusted. Safety in operation is also sacrificed by the necessity of working with flammable gas under pressure.

In contrast to known technology, the present process represents important advantages of the teachings of the prior art as exemplified by the Blanchard et al. and Brace disclosures.

It is an object of the present invention to produce a reactant addition product of perfluoroalkyl iodides and gaseous halogenated olefins which product is formed at or below atmospheric pressure.

SUMMARY OF THE INVENTION

An improved process is disclosed for the addition of perfluoroalkyl iodides of the formula:

$$C_nF_{2n+1}I \qquad (I)$$

wherein $n$ is an integer of 4 – 14, preferably 6 – 10, in which the perfluoro group may be straight or branched chained, to halogenated olefins to form halogenated end products of the formula:

$$C_nF_{2n+1}-(\underset{X_3}{\underset{|}{C}}-\underset{X_4}{\underset{|}{C}})_y-I \qquad (II)$$

wherein $X_1$, $X_2$, $X_3$ and $X_4$ represent an alkyl, hydrogen, chlorine or fluorine; at least a single X comprises chlorine or fluorine and $y$ is an integer from 1 to 10. It is desirable that the combination of $X_1$, $X_2$, $X_3$ and $X_4$ represent no more than two alkyl groups. Thus most desirably two of the groups will be fluorine or chlorine alone or either fluorine or chlorine as well as hydrogen or alkyl. The alkyl groups employed, methyl, ethyl, propyl and butyl are most preferably methyl or ethyl.

The gaseous halogenated olefins will contain at least one fluorine or chlorine atom and may contain only carbon and the halogen as in the case of tetrafluoroethylene. Both of the starting iodide and olefin may contain various mixtures of these compounds.

Telomerization in the addition reaction may or may not take place, which factor is determined by the choice of starting materials.

The technique utilized herein is carried out either at atmospheric pressure or under vacuum conditions. Most preferably, the reaction is at atmospheric pressure bypassing use of expensive equipment.

The process comprises bubbling the gaseous halogenated olefin, or mixtures thereof, into the perfluoroalkyl iodide and in the presence of a free radical generating catalyst such as benzoyl peroxide.

DETAILED DESCRIPTION OF THE INVENTION

In the process of the present invention, the halogenated olefins are gaseous at the reaction temperature while the perfluoroalkyl iodides employed as the starting materials must be liquid at reaction temperatures.

In the present context halogen is defined to mean only fluorine or chlorine.

Employing the reactant materials of the liquid perfluoroalkyl iodide and the gaseous halogenated olefin under the reaction conditions disclosed herein, a product is produced that may be free of telomers or may contain telomers. An important factor of whether telomerization takes place is the choice of starting reactant materials. In other words, by judiciously choosing a specific liquid perfluoroalkyl iodide gaseous halogenated olefin combination, telomerization may not take place and a one-to-one adduct will be formed.

As disclosed herein, perfluoroalkyl iodides are of the following formula:

$$C_nF_{2n+1}I$$

wherein $n$ is an integer from 4 to 14 and preferably 6 to 10, in which the perfluoro group may be straight or branched chains.

Into the liquid perfluoroalkyl iodide containing the free radical generating catalyst, a gaseous halogenated olefin is introduced. The requirement of the gaseous olefin is that it contain at least one fluorine constituent and be gaseous at the employed operating conditions within the range of 50°–220°C. Generally, the olefins employed may be substituted ethylene containing at least one fluorine or chlorine atom and may be further substituted by additional fluorine atoms, halogen, alkyl, preferably lower alkyl of 1 to 4 carbon atoms, i.e., methyl, ethyl, propyl, and butyl. Most desirably the olefin will contain no more than two alkyl groups with the preferred alkyl groups being methyl or ethyl. A preferred example on the basis of the addition reaction product is tetrafluoroethylene.

In order to initiate the reaction, a necessary component is a free radical generating catalyst such as the type employed by Brace in U.S. Pat. No. 3,145,222. Typical of these free radical generators are 2,2'-azobisisobutyronitrile, acyl peroxides, di-tert-butyl peroxide and benzoyl peroxide.

The resulting product from the source materials is of the formula:

$$C_nF_{2n+1}-\begin{pmatrix} X_1 & X_2 \\ | & | \\ C-C \\ | & | \\ X_3 & X_4 \end{pmatrix}_y-I \quad (II)$$

wherein $X_1$, $X_2$, $X_3$ and $X_4$ represent an alkyl, hydrogen or halogen, the combination of $X_1$, $X_2$, $X_3$ and $X_4$ desirably representing no more than two alkyl groups, at least a single X comprises fluorine or chlorine and $y$ is an integer from 1 to 10. A requirement in this process is that halogenated olefin be gaseous under the operating conditions while the perfluoroalkyl iodide be liquid at the reaction temperature. Generally, operating temperatures of 50° to 220° are suitable, although temperatures below 100°C are more desirable. It is most preferable that atmospheric pressure conditions be employed in perfluoroalkyl iodide liquid and thus pressurized equipment is totally unnecessary. While use of partial vacuum conditions obtains similar reactant results, such operating conditions are less desirable from the standpoint of increased equipment cost.

Generally, the flow of gaseous halogenated olefin is into the bottom of a reaction mixture of perfluoroalkyl iodide and a free radical generating catalyst, preferably adjusted to a slight excess over the rate it reacts for maximum efficiency. The substantial completion of the reaction is indicated when the rate of absorption of the halogenated olefin has practically ceased. Following completion of the reaction, the reaction mixture is separated into its constituent parts, generally by fractional distillation.

Telomerization may or may not take place under the influence of the source materials and the reactant conditions disclosed herein. Illustratively, the following source material, tetrafluoroethylene, will cause the telomer product to be formed, while the following reactant materials, vinyl fluoride, vinylidene fluoride, have shown nontelomer products to be formed.

As previously set forth, simply, the process requires bubbling the gaseous halogenated olefin or mixture through the liquid reaction mixture of free radical generating catalyst and liquid perfluoroalkyl iodide maintaining an atmosphere pressure within the operating temperature of 50° to 220°C. The temperature employed within the disclosed range will be chosen so that free radical generation occurs with the employed catalyst. The liquid perfluoroalkyl iodide need not be liquid over the entire temperature range disclosed, but will be a liquid under the chosen operating temperature within the range of 50° to 220°C.

Reaction times may be varied within wide limits and generally times of 1 to about 20 hours are suitable. In most instances, a period of about 2 hours to about 10 hours is preferred. Two hours is generally sufficient to allow a substantial portion of the starting perfluoroalkyl iodide to be consumed and, practically speaking, 3 to 4 hours may bring substantial reaction completion.

A broad range of free radical generating catalysts are operable and desirable in the present disclosure, such as those disclosed by Brace in U.S. Pat. No. 3,145,222. Generally speaking, amounts of catalyst of 0.001 to 0.1 mol per mol of perfluoroalkyl iodide are satisfactory with about 0.05 mol generally preferred. Greater amounts of catalyst could be employed but no significant advantage is realized.

Compounds obtained by the process of this invention are useful intermediates in the production of many products which possess valuable surface active properties. Products with such surface active properties, for example, have found wide use as components of textile finishes which impart oil and/or water repellent qualities to textile fabrics impregnated with such finishes. Also, the compounds could be further reacted with ethylene and utilized in the preparation of alcohols . . . (U.S. Pat. No. 3,283,012), of methacrylate esters (U.S. Pat. No. 3,239,557), of amines (Fr. Pat. No. 1,532,284), nitriles (Fr. Pat. No. 1,560,544) and malonic esters (U.S. Pat. No. 478,116).

While the process is primarily intended to be carried out at normal atmospheric pressure, it is, of course, apparent that pressures less than atmospheric may likewise be employed within the teachings of the invention provided. However, it is required that the perfluoroalkyl iodide remain liquid at such lesser pressure. The complexity of the equipment required, the pressure control and the like, make this alternative less desirable than operation under normal atmospheric pressure conditions.

In the following examples, parts are by weight and the relationship between parts by weight and parts by volume is as that of grams to cubic centimeters unless otherwise indicated.

EXAMPLE 1

A 25 ml flask is fitted with thermometer, gas inlet tube, and condenser. The flask is charged with 100 parts of 1-iodoperfluoroheptane and one part of benzoyl peroxide and brought to 90°–95°C before addition of gaseous tetrafluoroethylene. This gas is bubbled through the mixture for about 9 hours at which time the tetrafluoroethylene absorption has slowed to a point indicating that the reaction has ceased. The reaction mixture is then allowed to cool to room temperature. The compound $C_7F_{15}(CF_2CF_2)I$ is obtained in a 9.7% yield (VPC analysis) with lesser amounts of telomeric products.

EXAMPLE 2

The general procedure of Example 1 is followed except 1-iodoperfluorodecane is utilized and a stoichiometric equivalent amount of tetrafluoroethylene to obtain $CF_3(CF_2)_{11}I$ as an addition product.

EXAMPLES 3 and 4

The procedure of Example 1 was repeated employing a benzoyl peroxide catalyst and an operating temperature of about 95°. The perfluoroalkyl iodide, fluorinated olefin and addition product were as follows:

| Perfluoroalkyl Iodide | Olefin | Addition Product | bp/mm Hg. |
|---|---|---|---|
| $C_7F_{15}I$ | $CH_2=CHF$ | $C_7F_{15}CH_2CHFI$ | 86–7°/23 |
| $C_7F_{15}I$ | $CH_2=CF_2$ | $C_7F_{15}CH_2CF_2I$ | 80°/23 |

The products were identified by microanalysis and MNR.

While the invention has been explained by detailed description of certain specific embodiments, it is understood that various modifications and substitutions can be made in any of them within the scope of the appended claims which are intended also to include equivalents of such embodiments.

EXAMPLE 5

A 25 ml pear shaped flask fitted with thermometer condenser and gas inlet tube is charged with 14.88 parts of perfluoroheptyl iodide and 0.15 parts of benzoyl peroxide. The flask is heated to 90°C and vinyl chloride added at a rate slightly faster than it reacts, keeping the temperature at 90°–95°C. The disappearance of perfluoroheptyl iodide and the increase in two product peaks is followed by VPC. When all of the starting iodide is gone, the reaction is discontinued and the two products isolated by fractional distillation. The lower boiling product, boiling at 82°/10 mm weighs 4.25 parts and is identified by mass spectral analysis as 1-iodo-1-chloro-1,2,2-trihydroperfluorononane. The higher boiling product, boiling at 100°–103°/1 mm, weighs 9.48 parts and is identified by mass spectral analysis as the next higher telomer 1-iodo-1,3-dichloro-1,2,2,3,4,4,-hexahydroperfluoroundecane. There is VPC evidence that the next higher telomer may be present in the distillation residue.

What is claimed is:

1. A process for the addition of perfluoroalkyl iodides of the formula $C_nF_{2n+1}I$, wherein $n$ is an integer of 4–14, which are liquid at reaction temperature, to halogenated olefins which are gaseous at the employed reaction temperature, which comprises bubbling said olefin through said liquid iodide, in the presence of a free radical generating catalyst, at atmospheric or less than atmospheric pressure, at a reaction temperature of about 50°C to about 220°C, and recovering the reaction addition product.

2. A process for the addition of perfluoroalkyl iodides of the formula $C_nF_{2n+1}I$, wherein $n$ is an integer of 4–14, which are liquid at reaction temperature, to halogenated olefins which are gaseous at reaction temperature, which comprises bubbling said olefin through said liquid iodide, said liquid iodide containing a catalytic amount of a free radical generating catalyst, at atmospheric pressure, at a reaction temperature of about 50°C to about 220°C, and recovering the then formed reaction addition product.

3. The process of claim 2 wherein said olefin is of the formula $CX_1CX_3 = CX_2X_4$ wherein $X_1$, $X_2$, $X_3$, $X_4$ represents hydrogen, an alkyl of 1 to 4 carbon atoms chlorine or fluorine, wherein $X_1$, $X_2$, $X_3$, $X_4$ represents not more than two alkyl groups, and $X_1$, $X_2$, $X_3$, $X_4$ represents at least one fluorine atom.

4. The process of claim 2 wherein $n$ is an integer from 6 to 10.

5. The process of claim 3 wherein $n$ is an integer of 6 to 10.

6. The process of claim 5 wherein said olefin contains chlorine.

7. The process of claim 5 wherein said olefin contains fluorine.

* * * * *